United States Patent

Babin et al.

Patent Number: 6,140,340
Date of Patent: Oct. 31, 2000

[54] DERIVATIVES OF 2-[3-PHENYL-2-PROPENYL]-1,2,3,4-TETRAHYDRO ISOQUINOLINE, THEIR PROCESS AND THEIR USE AS FUNGICIDES

[75] Inventors: Didier Babin, Montigny; Abdel Karim Braham, Saint Denis, both of France; Stephen Hawser, Verbagna; Khalid Islam, Trecallo Como, both of Italy

[73] Assignee: Hoechst Marion Roussel, France

[21] Appl. No.: 09/412,011

[22] Filed: Oct. 4, 1999

[30] Foreign Application Priority Data

Oct. 6, 1998 [FR] France .................... 98 12483
Aug. 26, 1999 [FR] France .................... 99 10811

[51] Int. Cl.$^7$ .................. A61K 31/47; C07D 401/14
[52] U.S. Cl. ............... 514/307; 546/15; 546/148
[58] Field of Search ................... 546/139, 148, 546/15; 514/307

[56] References Cited

U.S. PATENT DOCUMENTS 2,813,872  11/1957  Schmutz .................. 546/139

FOREIGN PATENT DOCUMENTS 0050298  4/1982  European Pat. Off. .
0121753  10/1984  European Pat. Off. .

*Primary Examiner*—Zinna Northington Davis
*Attorney, Agent, or Firm*—Bierman, Muserlian and Lucas

[57] ABSTRACT

Derivatives of 2-[3-phenyl-2-propenyl]-1,2,3,4-tetrahydro-isoquinoline compounds of the formula in all their possible stereoisomer forms as well as their mixtures

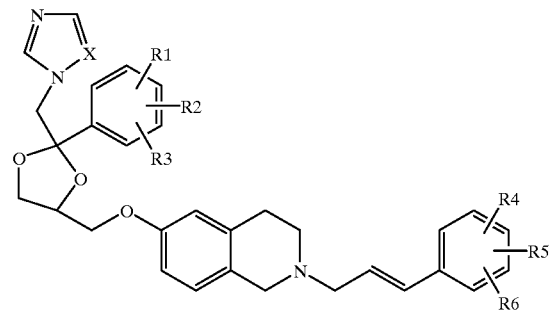

wherein X is nitrogen or —CH═, R1, R2, —R3, R4, R5, R6 are individually selected from the group consisting of a) hydrogen, halogen, alkyl, O-alkyl, $$\overset{(O)_n}{\underset{\uparrow}{S}}\text{-alkyl,}$$

alkenyl, O-alkenyl, $$\overset{(O)_n}{\underset{\uparrow}{S}}\text{-alkenyl,}$$

alkynyl, O-alkynyl, $$\overset{(O)_n}{\underset{\uparrow}{S}}\text{-alkynyl}$$

of up to 8 carbons, optionally substituted by at least one halogen, n is an integer of 0, 1 or 2, b) —NO$_2$, —NH$_2$ or —C≡N, R1, R2, R3, R4, R5 and R6 being able to form rings in pairs, as well and their non-toxic acid addition salts useful as fungicides.

14 Claims, No Drawings

DERIVATIVES OF 2-[3-PHENYL-2-PROPENYL]-1,2,3,4-TETRAHYDRO ISOQUINOLINE, THEIR PROCESS AND THEIR USE AS FUNGICIDES

OBJECTS OF THE INVENTION

It is an object of the invention to provide the novel compounds of formula I and their non-toxic, pharmaceutically acceptable acid addition salts and a process for their preparation.

It is another object of the invention to provide novel fungicidal compositions and a method of combatting fungi.

These and other objects and advantages of the invention will become obvious from the following detailed description.

THE INVENTION

The novel compounds of the invention are selected from the group consisting of a compound of the formula in all their possible stereoisomer forms as well as their mixtures

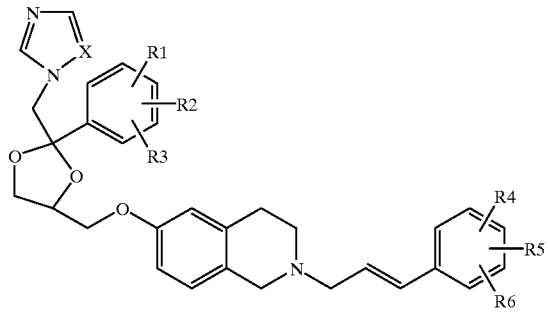

I wherein X is nitrogen or —CH═, R1, R2, R3, R4, R5, R6 are individually selected from the group consisting of a) hydrogen, halogen, alkyl, O-alkyl,

S-alkyl, alkenyl, O-alkenyl,

S-alkenyl, alkynyl, O-alkynyl,

S-alkynyl of up to 8 carbons, optionally substituted by at least one halogen, n is an integer of 0, 1 or 2, b) —NO$_2$, —NH$_2$ or —C≡N, R1, R2, R3, R4, R5 and R6 being able to form rings in pairs, as well as their non-toxic acid addition salts.

Preferably, the compounds are of the cis structure at the level of the dioxolane ring.

Examples of suitable acids for formation of the non-toxic, pharmaceutically acceptable acid addition salts are hydrochloric acid, hydrobromic acid, sulfuric acid, phosphoric acid, formic acid, acetic acid, trifluoroacetic acid, propionic acid, benzoic acid, citric acid, maleic acid, fumaric acid, succinic acid, tartaric acid, alkane sulfonic acids, such as methane or ethane sulfonic acids, arylsulfonic acids such as benzene or para toluenesulfonic acids.

Examples of alkyl are methyl, ethyl, propyl, isopropyl, n-butyl, isobutyl, tert.-butyl, decyl and dodecyl. Examples of alkenyl are vinyl and allyl and examples of alkynyl are ethynyl and propynyl. Examples of cycloalkyl include cyclobutyl, cyclopentyl and cyclohexyl. Examples of halogen are fluorine, chlorine and bromine.

A preferred group of compounds of the invention are compounds of the formula

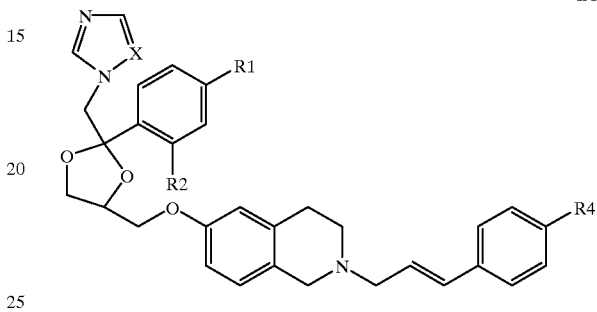

IA wherein X, R1, R2 and R4 are defined as above.

Among the preferred compounds of formula I are those wherein X is —CH═, those wherein R1 and R2 are halogen, those wherein R4 is halogen and those wherein R1, R2 and R4 are halogen. Especially preferred is the compound of Example 1 and particularly its cis (+) diastereoisomer described in Example 2.

The process for the preparation of the compounds of formula I comprises reacting a compound of the formula

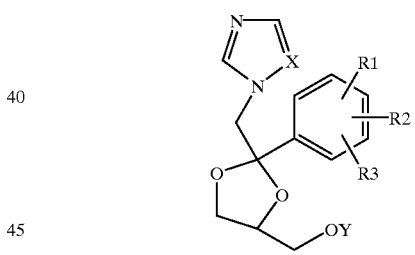

II wherein Y is mesyl or tosyl and the other substituents are defined as above with a compound of the formula

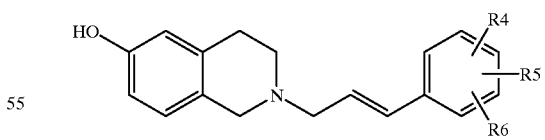

III wherein the substituents are defined as above to obtain the corresponding compound of formula I.

The products of formula II used as starting products are products which are known in a general fashion and which can be prepared according to the process indicated in J. Med. Chem., 1979 Vol. 22 (8), pp. 1003.

The compounds of formulae III and IV are novel and are an object of the invention.

The compounds of formula III may be prepared by the following reaction scheme

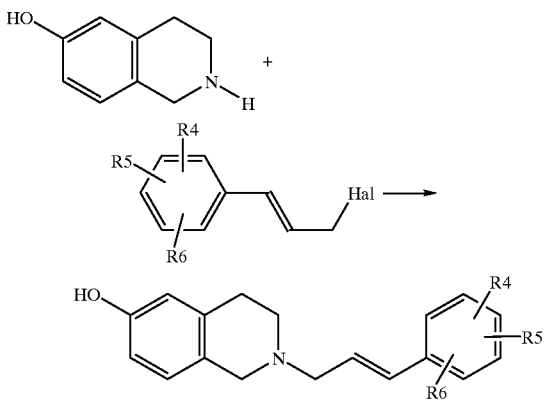

The compounds of formula I may be resolved by known procedures.

An alternate process for the preparation of compounds of formula I comprises reacting a compound of the formula

IV

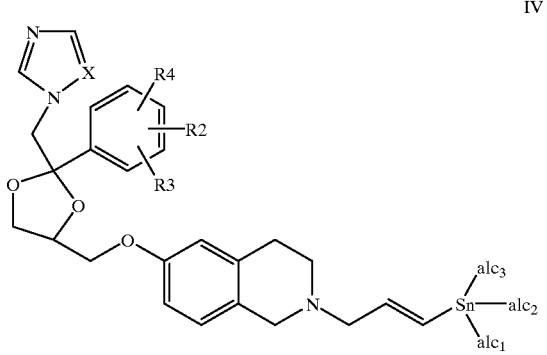

wherein $alc_1$, $alc_2$ and $alc_3$ are individually alkyl of up to 8 carbon atoms and X, R2, R3 and R4 are defined as above with a compound of the formula

V

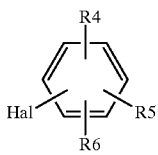

wherein R4, R5 and R6 are defined as above and Hal is halogen, preferably bromine or iodine to obtain a compound of formula I.

The fungicidal compositions of the invention are comprised of a fungicidally effective amount of a compound of formula I or a salt thereof and an inert pharmaceutical carrier. Examples of the pharmaceutical composition are plain or sugar-coated tablets, gelatin capsules, granules, suppositories, injectable preparations, ointments, creams or gels.

The fungicidal compositions are useful particularly on *Candida albicans* and other Candida such as *Candida glabrata, krusei, tropicalis, pseudotropicalis* and *parapsilosis*, on *Aspergillus fumigatus, Aspergillus flavus, Aspergillus niger, Cryptococcus neoformans, Microsporum canis, Trichophyton rubrun, Trichophyton mentagrophyte* and to combat particularly digestive, urinary, vaginal or cutaneous candidosis, cryptococcosis, for example, neuromeningeal, pulmonary or cutaneous cryptococcosis, bronchopulmonary and pulmonary aspergillosis and invasive aspergillosis of the immunodepressive system. The compositions can also be used in the prevention of mycotic affections in congenital or acquired immunological suppressions.

The novel method for combatting fungal infections in warm-blooded animals comprises administering to warm-blooded animals a fungicidally effective amount of a compound of formula I or an acid addition salt thereof. The compositions can be administered by buccal, rectal, parenteral route, or by local route as a topical application on the skin and mucous membranes, but the preferred route is the buccal route. The usual daily dose is 2 to 15 mg/kg depending on the method of administration, the condition treated and the specific compound.

Examples of carriers include talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

These compositions can also be presented in the form of a powder intended to be dissolved extemporaneously in an appropriate vehicle, for example, apyrogenic sterile water.

In the following examples, there are described several preferred embodiments to illustrate the invention. However, it is to be understood that the invention is not intended to be limited to the specific embodiments.

PREPARATION 1

(E)-2-[3-(4-chlorophenyl)-2-propenyl]-1,2,3,4-tetrahydro-6-isoquinolinol

A mixture of 2 g of 1,2,3,4-tetrahydro-6-isoquinolinol and 2.5 g of (E)-1-chloro-4-[3-chloro-1-propenyl]-benzene, 2 g of potassium carbonate and 50 ml of DMF was stirred for 36 hours at 25° C. and then the DMF was evaporated off under reduced pressure. The residue was taken up in a mixture of methylene chloride and water and filtration was carried out to obtain 2.5 g of the desired product melting at 233–234° C.

EXAMPLE 1

Cis-(±)-2-[3-(4-chlorophenyl)-2-(E)-propenyl]-6-[[2-(2,4-dichlorophenyl)-2-(1H-imidazol-1-ylmethyl)-1,3-dioxolan-4-yl]methoxy]-1,2,3,4-tetrahydro-isoquinoline A mixture of 2 g of the product of Preparation 1, 3.1 g of Cis-(±)-2-(2,4-dichlorophenyl)-2-(1H-imidazol-1-ylmethyl)-1,3-dioxolane-4-methanol methane sulfonate, 50 ml of toluene, 4 ml of a 50% solution of sodium hydroxide and 300 ml of tribenzylammonium chloride ($C_6H_5CH_2$ $Et_3N^+$ $Cl^-$ was refluxed for 3.5 hours, followed by cooling. The toluene layer was separated and the aqueous layer was extracted with toluene. The two toluene layers were combined, dried, filtered and evaporated. The product was recrystallized from a mixture of ethyl ether and ethyl acetate to obtain 3.2 g of the desired product 127~129° C.

Analysis C 62.91%
H = 4.95%
N = 6.88%

-continued

Cl = 17.41%
O₃ = 7.86%

EXAMPLE 2

Cis-(+)-2-[3-(4-chlorophenyl)-2-(E)-propenyl]-6-[[2-(2,4-dichlorophenyl)-2-(1H-imidazol-1-ylmethyl)-1,3-dioxolan-4-yl]methoxy]-1,2,3,4-tetrahydro-isoquinoline A mixture of 480 mg of cis(+)-2-(2,4-dichlorophenyl)-2-(1H-imidazol-1-ylmethyl)-1,3-dioxolane-4-methanol 4-methylphenyl-sulfonate, 300 mg of the product of Preparation 1, 276 mg of potassium carbonate and 10 ml of DMF was heated at 90° C. for 3 hours and 30 minutes. The reaction medium was stirred at ambient temperature overnight, followed by filtering and rinsing with DMF. The filtrate was dried at 40° C. under reduced pressure and the residue was taken up in methylene chloride and water (50/50), stirred and decanted. The aqueous phase was extracted with methylene chloride and the combined organic phases were dried, filtered and evaporated to dryness at 35° C. The product was purified by chromatography on silica eluting with an ethyl acetate, methanol mixture 93/7. The crude product was triturated in 4 ml of an ethyl ether, ethyl acetate mixture 9/1, dried, washed with ethyl ether, followed by drying to obtain 338 mg of product which was purified by chromatography on silica eluting with an ethyl acetate, methanol mixture (93/7) to obtain 332 mg of the desired product melting at 110° C. and having $[\alpha]_D$=+12° (c=1% in methanol).

EXAMPLE 3

Cis (−)2-[3-(4-chlorophenyl)-2-(E)-propenyl]-6-[[2-(2,4-dichlorophenyl)-2-(1H-imidazol-1-ylmethyl)-1,3-dioxolan-4-yl]-methoxy]-1,2,3,4-tetrahydro-isoquinoline Using the procedure of Example 2, cis-(−)-2, (2,4-dichlorophenyl)-2-[(1H-imidazol-1-yl)-methyl]-1,3-dioxolan-4-methanol methylphenyl and the product of Preparation 1 were reacted to obtain the desired product melting at 120° C. and having a specific rotation of $[\alpha]_D$: −10° (c=1% in methanol).

PREPARATION 2

The starting products of Examples 2 and 3, namely Cis-(+)-2-(2,4-dichlorophenyl)-2-(1H-imidazol-1-ylmethyl)-1,3-dioxolane-4-methanol methyl toluene sulfonate, and the corresponding Cis(−) compound were prepared by chinal phase chromatography starting with the corresponding Cis ± (I) product to obtain the Cis isomer (+) $[\alpha]_D$=+7° and the Cis isomer (−) $[\alpha]_D$=−7°.

EXAMPLE 4

A mixture of 0.3 mmol of ArX derivative, 1.5 ml (0.2 mmol) of the product of Preparation 3 and 1.5 ml of a (0.02 mmol) solution of $PdCl_2$ $(P\phi3)_2$ in DMF was heated at 65° C. for 4 hours 30 minutes. A solution of water, potassium fluoride, sodium acid carbonate (80-10-70) was added, followed by extraction with methylene chloride and drying to obtain the following products.

| | φ(Ru) (R5) (R6) | Formula | Mw | Expected Product | Mw | Formula |
|---|---|---|---|---|---|---|
| 5 | (2-bromothiazole) | C3H2BrNS | 164,02 | (structure with furan) | 583,54 | C29H28Cl2N4O3S (M+H)+ = 584+ |
| 6 | (iodobenzene) | C6H5I | 204,01 | (structure with phenyl) | 576,53 | C32H31Cl2N3O3 (M+H)+ = 577+ |
| 7 | (2-iodothiophene) | C4H3IS | 210,04 | (structure with thiophene) | 582,55 | C30H29Cl2N3O3S (M+H)+ = 583+ |

-continued

| | φ(Ru) (R5) (R6) | Formula | Mw | Expected Product | Mw | Formula |
|---|---|---|---|---|---|---|
| 8 | 3-iodotoluene structure | C7H7I | 218.04 | structure with 3-methylphenyl cinnamyl group | 590.56 | C33H33Cl2N3O3 (M+H)+ = 591+ |
| 9 | 2-iodotoluene structure | C7H7I | 218.04 | structure with 2-methylphenyl cinnamyl group | 590.56 | C33H33Cl2N3O3 (M+H)+ = 591+ |
| 10 | 4-iodophenol structure | C6H5IO | 220.01 | structure with 4-methylphenyl cinnamyl group | 592.54 | C32H31Cl2N3O4 (M+H)+ = 593+ |

-continued
| | φ(Ru) (R5) (R6) | Formula | Mw | Expected Product | Mw | Formula |
|---|---|---|---|---|---|---|
| 11 | 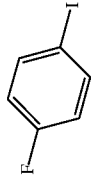 | C6H4FI | 222,00 | 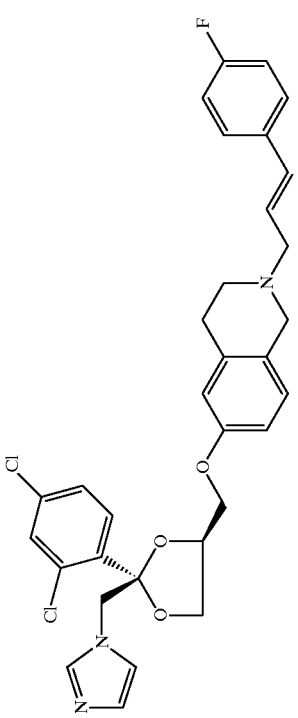 | 594,52 | C32H30Cl2FN3O3 (M+H)+ = 594+ |
| 12 | 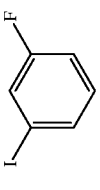 | C6H4FI | 222,00 | 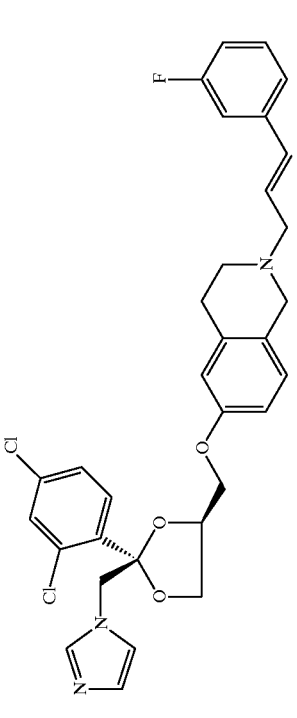 | 594,52 | C32H30Cl2FN3O3 (M+H)+ = 594+ |
| 13 | 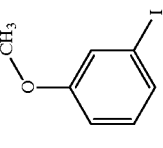 | C7H7IO | 234,04 | 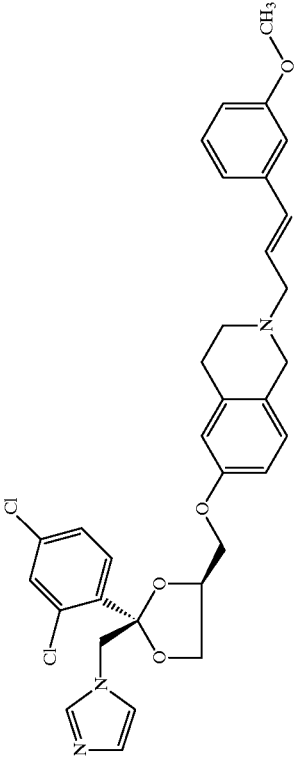 | 606,55 | C33H33Cl2N3O4 (M+H)+ = 606+ |

| | φ(Ru) (R5) (R6) | Formula | Mw | Expected Product | Mw | Formula |
|---|---|---|---|---|---|---|
| 14 | 4-iodoanisole (CH3-O-C6H4-I) | C7H7IO | 234,04 | [structure with 4-methoxyphenyl cinnamyl group] | 606,55 | C33H33Cl2N3O4 (M+H)+ = 606+ |
| 15 | 2-fluoro-4-iodoaniline (NH2, F, I on benzene) | C6H5FIN | 237,02 | [structure with 3-fluoro-4-methylphenyl cinnamyl group] | 609,53 | C32H31Cl2FN4O3 (M+H)+ = 609+ |
| 16 | 1-chloro-3-iodobenzene | C6H4ClI | 238,46 | [structure with 3-chlorophenyl cinnamyl group] | 610,97 | C32H30Cl3N3O3 (M+H)+ = 610+ |

-continued

| | φ(Ru) (R5) (R6) | Formula | Mw | Expected Product | Mw | Formula |
|---|---|---|---|---|---|---|
| 17 | 3,4-difluoro-iodobenzene | C6H3F2I | 239,99 | [structure] | 612,51 | C32H29Cl2F2N3O3 (M+H)+ = 612+ |
| 18 | 4-ethyl-iodobenzene | C7H7IO | 234,04 | [structure] | 618,61 | C35H37Cl2N3O3 (M+H)+ = 618+ |
| 19 | 5-iodo-benzo[1,3]dioxole | C7H5IO2 | 248,02 | [structure] | 620,54 | C33H31Cl2N3O5 (M+H)+ = 620+ |

| | φ(Ru) (R5) (R6) | Formula | Mw | Expected Product | Mw | Formula |
|---|---|---|---|---|---|---|
| 20 | naphthyl-I | C10H7I | 254,07 | (naphthalen-1-yl structure) | 626,59 | C36H33Cl2N3O3 (M+H)+ = 626+ |
| 21 | 3-Cl-4-F-C6H3-I | C6H3ClFI | 256,45 | (3-Cl-4-F-phenyl structure) | 628,96 | C32H29Cl3FN3O3 (M+H)+ = 628+ |
| 22 | 4-(C(CH3)2)-C6H4-I | C10H13I | 260,12 | (4-isopropyl-phenyl structure) | 632,64 | C36H39Cl2N3O3 (M+H)+ = 632+ |

-continued
| | φ(Ru) (R5) (R6) | Formula | Mw | Expected Product | Mw | Formula |
|---|---|---|---|---|---|---|
| 23 | 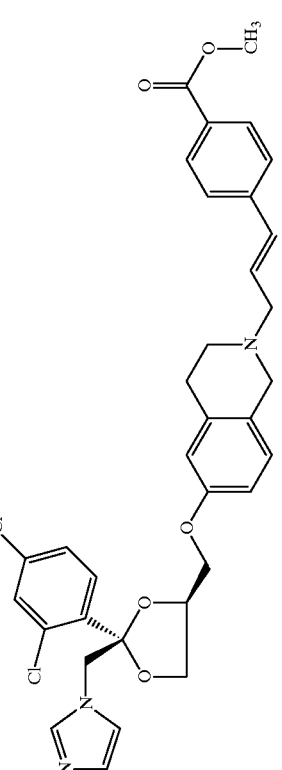 | C8H7IO2 | 262,05 | 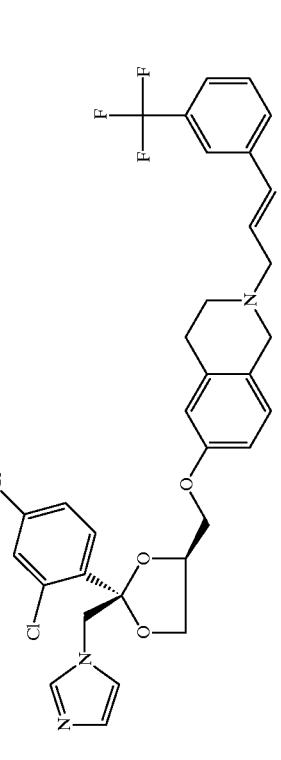 | 634,57 | C34H33Cl2N3O5 (M+H)⁺ = 634⁺ |
| 24 | | C7H4F3I | 272,01 | | 644,53 | M33H30Cl2F3N3O3 (M+H)⁺ = 644⁺ |
| 25 | 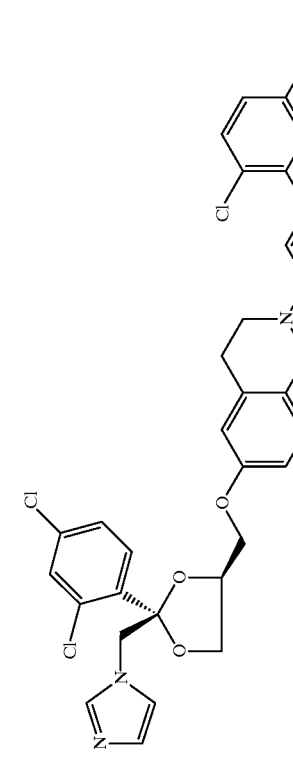 | C6H3Cl2I | 272,90 | | 645,42 | C32H29Cl4N3O3 (M+H)⁺ = 644⁺ |

| | φ(Ru) (R5) (R6) | Formula | Mw | Expected Product | Mw | Formula |
|---|---|---|---|---|---|---|
| 26 | 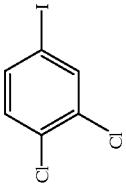 | C6H3Cl2I | 272,90 | 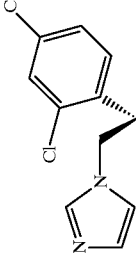 | 645,42 | C32H29Cl4N3O3 (M+H)+ = 644+ |
| 27 | 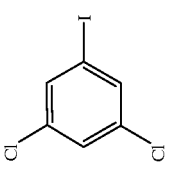 | C6H3Cl2I | 272,90 | 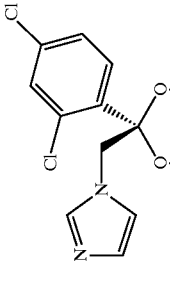 | 645,42 | C32H29Cl4N3O3 (M+H)+ = 644+ |
| 28 | 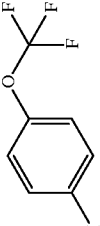 | C7H4F3IO | 288,01 | 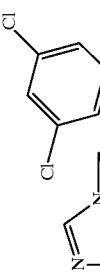 | 660,53 | C33H30Cl2F3N3O4 (M+H)+ = 660+ |

Using the above procedure, the following products were also prepared:

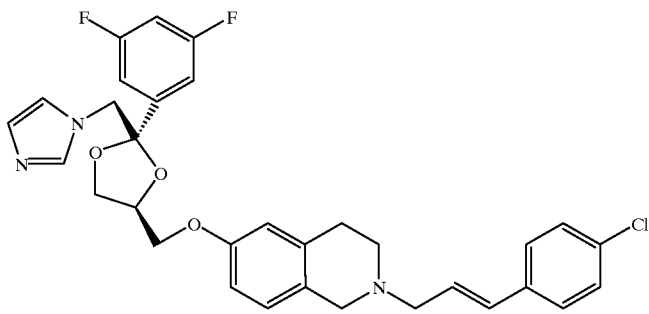

Rf: 0.30 ethyl acetate-triethylamine 95-5

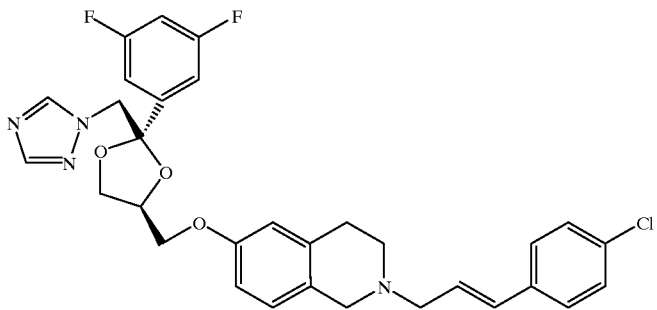

PREPARATION 3

Cis(±)6-[[2-(2,4dichlorophenyl)-2-(1H-imidazol-1-ylmethyl)-1,3-dioxolan-4-yl]-methoxy]-1,2,3,4-tetrahydro-2-[3-tributylstannyl)-2(E)-propenyl]-isoquinoline Stage A: 3-(tributylstannyl)-2(E)-propen-1-ol 12 g of methyl 3-(tributylstannyl)-2(E)-propenoate were dissolved in 100 ml of THF and after the reaction medium was cooled to −78° C., 67 ml of dibutylaluminum hydride were added. The temperature was taken to 0° C., followed by pouring into methanol. Water was added and the mixture was stirred overnight. The aluminum salts were filtered off, washed with ethyl acetate and the organic phases were decanted, dried and, concentrated to obtain 9 g of product which was purified by chromatography eluting with a hexane ethyl acetate mixture 8/2 to obtain 7.25 g of the desired product.

Stage B: (3-bromo-1-(E)-propenyl)tributyl-stannane

A solution of 5.5 g of triphenylphosphine in 10 ml of methylene chloride was added dropwise at 0° C. over 30 minutes into a solution of 5.2 g of the product of stage A in 50 ml of methylene chloride and 6 g of carbon tetrabromide. The reaction medium was held at 0° C. for one hour followed by pouring into water and extracting with methylene chloride, drying, followed by chromatography on silica eluting with heptane to obtain 5.06 g of the desired product.

Stage C: Cis(±)6-[[2-2,4dichlorophenyl)-2-(1H-imidazol-1-yl-methyl)-1,3-dioxolan-4-yl]-methoxy]-1,2,3,4-tetrahydro-2-[3-tributylstannyl)-2(E)-propenyl]-isoquinoline A solution of 5.06 g of product of Stage B and 20 ml of acetone was added dropwise with stirring and a nitrogen atmosphere into a mixture of 5.68 g of Cis (±)6-[[2-(2,4dichlorophenyl)-2-(1H-imidazol-1-yl-methyl)-1,3-dioxolan-4-yl]-methoxy]-1,2,3,4-tetrahydro-isoquinoline prepared in Preparation 4, 1.5 g of Ag2, 100 ml of acetone and 50 ml of DMF. The reaction mixture was held at ambient temperature overnight followed by filtering, taking up in water, extracting with ethyl acetate, purifying by chromatography on silica (eluent : methylene chloride, methanol (95-5) to obtain 6.66 g of the desired product.

PREPARATION 4

Cis (±)6-[[2-(2,4dichlorophenyl)-2-(1H-imidazol-1-yl-methyl)-1,3-dioxolan-4-yl]-methoxy]-1,2,3,4-tetrahydro-isoquinoline Stage A:

A suspension of 5.8 g of 1,2,3,4-tetrahydroisoquinoline 6-OH and 50 ml of THF was stirred for 15 hours at ambient temperature and then 11.13 g of diterbutyl dicarbonate in 25 ml of THF were added at 20° C. followed by pouring into an ice-cooled solution of potassium acid carbonate. The mixture was extracted with ethyl acetate, dried, filtered and concentrated. The product was taken up in pentane, initiated and the crystals obtained were washed with pentane to obtain 9.26 g of the desired product melting at 114° C.

Stage B:

5.4 g of sodium hydride at 55=60% dispersed in oil were introduced over 20 minutes at ambient temperature into a solution of 24.63 g of the product of Stage A and 250 ml of DMF. The reaction mixture was taken to 55° C. for 2 hours and allowed to return to ambient temperature. 54.6 g of cis-(+)-2-(2,4-dichlorophenyl)-2-(1H-imidazol-1-yl-methyl)-1,3-dioxolane-4-methanol methane sulfonate were added and the reaction mixture was taken to 80° C. for 20 hours followed by stirring at ambient temperature for 72 hours. The mixture was poured onto ice, stirred for one hour, decanted, dried, filtered and concentrated to obtain 95.8 g of product which was chromatographed on silica eluting with a heptane acetone (6/4) mixture to obtain 45 g of the desired product which was used as is in the following stage.

Stare C: Cis (±)6-[[2-(2,4dichlorophenyl)-2-(1H-imidazol-1-yl-methyl)-1,3-dioxolan-4-yl)-methoxy]-1,2,3,4-tetrahydroisoquinoline.

45 g of the product of stage B in solution in 200 ml of ethyl acetate were cooled to 10° C. and 100 ml of a solution of 50 g of ice and 50 ml of a 12N solution of hydrochloric acid were added. The reaction mixture was stirred for 4 hours followed by concentrating under reduced pressure and taking up in ethyl acetate. The product was taken up in ethyl ether, triturated, separated, rinsed and dried to obtain 60.8 g of product which was poured into 250 ml of water followed by cooling and 50 ml of 28% ammonium hydroxide solution was poured in and the mixture was stirred for 30 minutes. 150 ml of methylene chloride were added and the reaction mixture was stirred for 30 minutes, extracted with methylene chloride, washed, dried, filtered and concentrated to obtain 35.68 g of the desired product.

Pharmaceutical Compositions

Tables were prepared containing 50 mg of the Product of Example 1 and sufficient excipient of starch, talc and magnesium stearate for a 1 g tablet.

Anti-fungal Activity of the Product of Example 1 or Product P.

Female mice weighing 18 to 22 g were used and a quantity of *Candida Albicans* 44858 was administered into a vein in the tail at the rate of $10^6$ CFU per mouse (CFU: colony forming unit). The mice were separated into 5 batches of 5 mice and they were treated in the following manner:

One Hour After Infection group 1: the mice were treated with product P at 25 mg/kg orally group 2: the mice were treated with product P intraperitoneally at the dose of 25 mg/kg group 3: the mice were treated orally with fluconazole at 25 mg/kg group 4: the mice were treated intraperitoneally with fluconazole at a dose of 25 mg/kg group 5: the mice did not receive any anti-fungal treatment.

The dead mice were counted over a period of 22 days.

Conclusion

The product showed an excellent activity at the dose used in the two administration methods. Moreover, the test was carried out with an administration of the order of those obtained with fluconazole. The same treatments were also effective in the "topical model" with dermal fungi, for example trichophyton, and in the sublethal model.

Minimal Inhibitory Concentration (MIC)

*Candida albicans* cells were prepared as indicated in the Journal of Antimicrobial Chemotherapy, Vol. 38, pp. 579–587 and were washed 3 times with a 0.1 M phosphate solution and used immediately to determine the minimal inhibitory concentration (MIC). The MICs were determined by modification of a microtitre plate according to the standard method of the laboratory clinical standards of the Comité National.

RPMI-1640, and L-glutamine buffered at pH7 with a 0.15 M solution of MOPS (3-[N-morpholino]propane sulfonic acid). *Candida albicans* cells ($1.5 \times 10_3$ cells/ml) were added to the wells of a 96-well plate containing RPMI-1640 and dilutions of anti-fungal agents. The results were read 48 hours after incubation at 35° C. and the MIC or the minimal inhibitory concentration which inhibited the growth of the Candida albicans cells was determined.

Minimal Fungicidal Concentration

After reading the MIC at 48 hours, the plates were shaken and 10 μl of well aliquot was removed from the wells which was placed on rectangular disks containing dextrose sugar. The plates were incubated for 48 hours at 35° C. and the minimal fungicidal concentration and the concentration of the antifungal agent at which the number of colony forming units was zero.

Various modifications of the products and method of the invention may be made without departing from the spirit or scope thereof and it is to be understood that the invention is intended to be limited only as defined in the appended claims.

What is claimed is:

1. A compound selected from the group consisting of a compound of the formula in all their possible stereoisomer forms as well as their mixtures

I wherein X is nitrogen or —CH═, R1, R2, R3, R4, R5, R6 are individually selected from the group consisting of a) hydrogen, halogen, alkyl, O-alkyl, $$\overset{(O)_n}{\underset{\uparrow}{\text{S-alkyl,}}}$$

alkenyl, O-alkenyl, $$\overset{(O)_n}{\underset{\uparrow}{\text{S-alkenyl,}}}$$

alkynyl, O-alkynyl, $$\overset{(O)_n}{\underset{\uparrow}{\text{S-alkynyl}}}$$

of up to 8 carbons, optionally substituted by at least one halogen, n is an integer of 0, 1 or 2, b) —NO$_2$, —NH$_2$ or —C≡N, R1, R2, R3 R4, R5 and R6 being able to form rings in pairs, as well and their non-toxic acid addition salts.

2. A compound of claim 1 having the formula

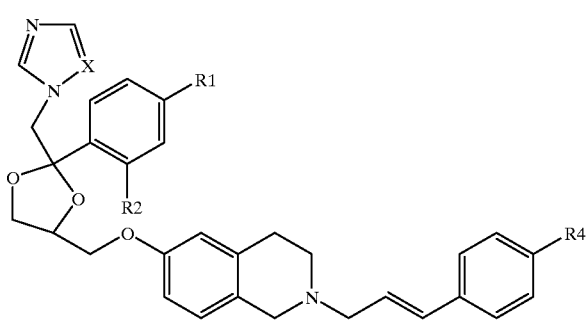

IA wherein X, R1, R2 and R4 are defined as in claim 1.

3. A compound of claim 1 wherein X is —CH=.

4. A compound of claim 1 wherein R1 and R2 are halogen.

5. A compound of claim 1 wherein R4 is halogen.

6. A compound of claim 1 wherein R1, R2 and R4 are chlorine.

7. A compound of claim 1 which is Cis-(±)-2-[3-2-(1H-imidazol- 1-ylmethyl)-1,3-dioxolan-4-yl]methoxy]-1,2,3,4-tetrahydro-isoquinoline.

8. A compound of claim 7 in its cis (+) enantiomer form.

9. A process for the preparation of a compound of claim 1 comprising reacting a compound of the formula

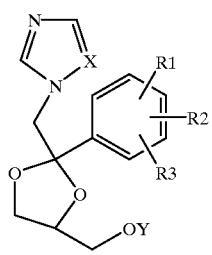

II wherein Y is mesyl or tosyl and the other substituents are defined as above with a compound of the formula

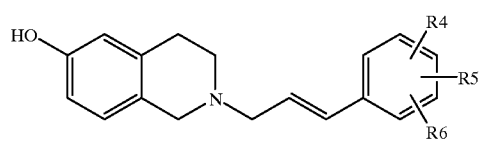

III wherein the substituents are defined as above to obtain the corresponding compound of formula I.

10. A process for the preparation of a compound of claim 1 comprising reacting a compound of the formula

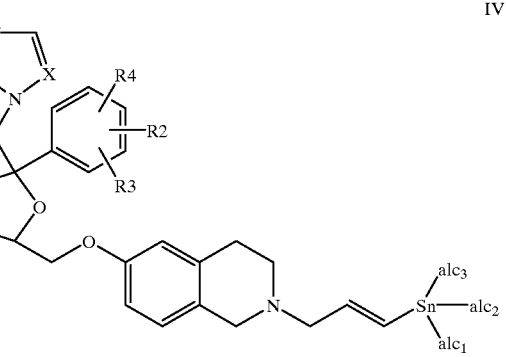

IV wherein $alc_1$, $alc_2$ and $alc_3$ are individually alkyl of up to 8 carbon atoms and X, $R_2$, $R_3$ and $R_4$ are defined as above with a compound of the formula

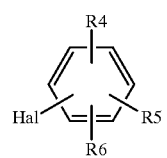

V wherein R4, R5 and R6 are defined as above and Hal is halogen to obtain the compound of claim 1.

11. A compound selected from the group consisting of a compound of the formula

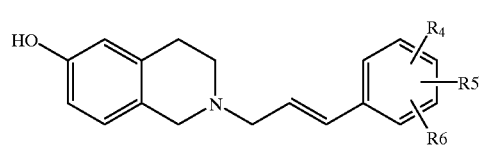

III and

-continued

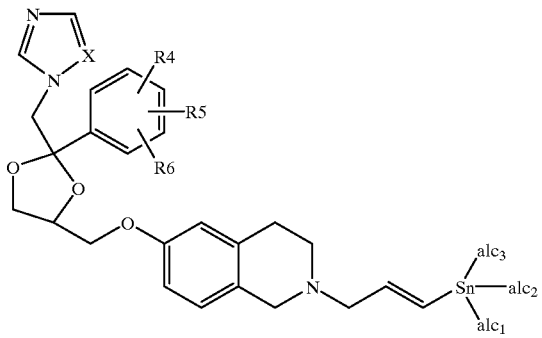

IV wherein X is nitrogen or —CH=, R2, R3, R4, R5, R6 are individually selected from the group consisting of a) hydrogen, halogen, alkyl, O-alkyl, $$\overset{(O)_n}{\underset{\uparrow}{\text{S-alkyl,}}}$$

alkenyl, O-alkenyl, $$\overset{(O)_n}{\underset{\uparrow}{\text{S-alkenyl,}}}$$

alkynyl, O-alkynyl, $$\overset{(O)_n}{\underset{\uparrow}{\text{S-alkynyl}}}$$

of up to 8 carbons, optionally substituted by at least one halogen, n is an integer of 0, 1 or 2, b) —NO$_2$, —NH$_2$ or —C≡N, R1, R2, R3 R4, R5 and R6 being able to form rings in pairs, as well and their non-toxic acid addition salts), alc$_1$, alc$_2$, and alc$_3$ are alkyl of up to 8 carbon atoms.

12. An antifungal composition comprising a fungicidally effective amount of a compound of claim 1 and a carrier.

13. A method of treating fungal infections in warm-blooded animals comprising administering to warm-blooded animals a fungicidally effective amount of a compound of claim 1.

14. A method of treating fungal infections in warm-blooded animals comprising administering to warm-blooded animals a fungicidally effective amount of a compound of claim 8.

* * * * *